US009403799B2

(12) United States Patent
Schadt et al.

(10) Patent No.: US 9,403,799 B2
(45) Date of Patent: *Aug. 2, 2016

(54) PYRIMIDINYL-PYRIDAZINONE DERIVATIVES FOR TREATING A DISEASE WHICH IS INFLUENCED BY INHIBITION OF MET KINASE

(71) Applicant: Merck Patent GmbH, Darmstadt (DE)

(72) Inventors: Oliver Schadt, Rodenbach (DE); Dieter Dorsch, Ober-Ramstadt (DE); Frank Stieber, Heidelberg (DE); Andree Blaukat, Schriesheim (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/602,921

(22) Filed: Jan. 22, 2015

(65) Prior Publication Data

US 2015/0133452 A1 May 14, 2015

Related U.S. Application Data

(62) Division of application No. 14/149,110, filed on Jan. 7, 2014, now Pat. No. 9,062,029, which is a division of application No. 13/565,914, filed on Aug. 3, 2012, now Pat. No. 8,658,643, which is a division of application No. 12/668,491, filed as application No. PCT/EP2008/005508 on Jul. 4, 2008, now Pat. No. 8,329,692.

(30) Foreign Application Priority Data

Jul. 12, 2007 (DE) .......................... 10 2007 032 507
Apr. 29, 2008 (WO) ................. PCT/EP2008/003473

(51) Int. Cl.
| | |
|---|---|
| A61K 47/02 | (2006.01) |
| A61K 9/08 | (2006.01) |
| A61K 9/19 | (2006.01) |
| C07D 417/10 | (2006.01) |
| C07D 451/06 | (2006.01) |
| C07D 409/14 | (2006.01) |
| C07D 405/14 | (2006.01) |
| C07D 453/02 | (2006.01) |
| C07D 413/10 | (2006.01) |
| C07D 403/14 | (2006.01) |
| C07D 403/10 | (2006.01) |
| C07D 401/10 | (2006.01) |
| C07D 401/14 | (2006.01) |
| C07D 413/14 | (2006.01) |
| C07D 417/14 | (2006.01) |
| A61K 31/501 | (2006.01) |
| A61K 31/506 | (2006.01) |

(Continued)

(52) U.S. Cl.
CPC ............ *C07D 403/10* (2013.01); *A61K 9/0014* (2013.01); *A61K 9/0019* (2013.01); *A61K 9/0031* (2013.01); *A61K 9/0048* (2013.01); *A61K 9/02* (2013.01); *A61K 9/06* (2013.01); *A61K 9/08* (2013.01); *A61K 9/2018* (2013.01); *A61K 31/501* (2013.01); *A61K 31/506* (2013.01); *A61K 31/5355* (2013.01); *A61K 31/5377* (2013.01); *A61K 31/55* (2013.01); *A61K 45/06* (2013.01); *A61K 47/02* (2013.01); *C07D 401/10* (2013.01); *C07D 401/14* (2013.01); *C07D 403/14* (2013.01); *C07D 405/14* (2013.01); *C07D 409/14* (2013.01); *C07D 413/10* (2013.01); *C07D 413/14* (2013.01); *C07D 417/10* (2013.01); *C07D 417/14* (2013.01); *C07D 451/06* (2013.01); *C07D 453/02* (2013.01); *A61K 9/19* (2013.01); *A61K 9/2826* (2013.01)

(58) Field of Classification Search
CPC ....... A61K 47/02; A61K 9/08; A61K 9/2826; A61K 9/19; A61K 9/0014; A61K 9/0019; A61K 31/506; A61K 31/5355; A61K 31/501; A61K 31/55; A61K 31/5377; A61K 45/06; C07D 417/10; C07D 417/14; C07D 451/06; C07D 409/14; C07D 405/14; C07D 453/02; C07D 413/10; C07D 413/14; C07D 403/14; C07D 401/10
USPC ................... 514/236.5, 252.02; 544/123, 298
See application file for complete search history.

(56) References Cited

U.S. PATENT DOCUMENTS

| | | | |
|---|---|---|---|
| 6,242,461 | B1 | 6/2001 | Goldstein |
| 6,403,586 | B1 | 6/2002 | Ohkuchi et al. |

(Continued)

FOREIGN PATENT DOCUMENTS

| | | |
|---|---|---|
| DE | 19604388 | 8/1997 |
| DE | 102005057924 | 6/2007 |

(Continued)

OTHER PUBLICATIONS

"Cancer" MedLine Plus (2009). Accessed Mar. 17, 2009. http://www.nlm.nih.gov/medlineplus/cancer.html.

(Continued)

*Primary Examiner* — James O Wilson
*Assistant Examiner* — Ebenezer O Sackey
(74) *Attorney, Agent, or Firm* — Millen White Zelano and Branigan, PC; Csaba Henter; Anthony Zelano

(57) ABSTRACT

Compounds selected from the group according to claim 1 are inhibitors of tyrosine kinases, in particular of Met kinase, and can be employed, inter alia, for the treatment of tumors.

20 Claims, No Drawings

(51) Int. Cl.

| | | |
|---|---|---|
| A61K 31/5355 | (2006.01) | |
| A61K 31/5377 | (2006.01) | |
| A61K 31/55 | (2006.01) | |
| A61K 45/06 | (2006.01) | |
| A61K 9/00 | (2006.01) | |
| A61K 9/02 | (2006.01) | |
| A61K 9/06 | (2006.01) | |
| A61K 9/20 | (2006.01) | |
| A61K 9/28 | (2006.01) | |

(56) References Cited

U.S. PATENT DOCUMENTS

| | | | |
|---|---|---|---|
| 8,071,593 | B2 | 12/2011 | Schadt et al. |
| 8,173,653 | B2 | 5/2012 | Dorsch et al. |
| 8,329,692 | B2 | 12/2012 | Schadt et al. |
| 8,580,781 | B2 | 11/2013 | Dorsch et al. |
| 8,658,643 | B2 * | 2/2014 | Schadt ............... C07D 401/10 514/236.5 |
| 2004/0152739 | A1 | 8/2004 | Hanau |
| 2004/0259863 | A1 | 12/2004 | Eggenweiler et al. |
| 2005/0107391 | A1 | 5/2005 | Cui et al. |
| 2007/0015771 | A1 | 1/2007 | Matteucci et al. |
| 2007/0043057 | A1 | 2/2007 | Matteucci et al. |
| 2007/0203136 | A1 | 8/2007 | Lu et al. |
| 2007/0265272 | A1 | 11/2007 | Cheng et al. |
| 2008/0293719 | A1 | 11/2008 | Dorsch et al. |
| 2009/0098181 | A1 | 4/2009 | Lu et al. |
| 2009/0124612 | A1 | 5/2009 | Albrecht et al. |
| 2010/0197690 | A1 | 8/2010 | Schadt et al. |
| 2010/0234354 | A1 | 9/2010 | Dorsch et al. |
| 2010/0273796 | A1 | 10/2010 | Dorsch et al. |
| 2010/0280030 | A1 | 11/2010 | Schadt et al. |
| 2010/0286390 | A1 | 11/2010 | Shigeta et al. |
| 2011/0034474 | A1 | 2/2011 | Dorsch et al. |
| 2011/0092498 | A1 | 4/2011 | Dorsch et al. |
| 2011/0098269 | A1 | 4/2011 | Becknell et al. |
| 2011/0112061 | A1 | 5/2011 | Hu et al. |
| 2011/0263596 | A1 | 10/2011 | Schadt et al. |
| 2011/0269957 | A1 | 11/2011 | Fandrick et al. |
| 2012/0028988 | A1 | 2/2012 | Sakamoto et al. |
| 2012/0040949 | A1 | 2/2012 | Berthel et al. |
| 2012/0295908 | A1 | 11/2012 | Schadt et al. |

FOREIGN PATENT DOCUMENTS

| | | |
|---|---|---|
| EP | 1061077 | 12/2000 |
| JP | 10259176 | 9/1998 |
| JP | 2001192384 | 7/2001 |
| WO | 03037349 | 5/2003 |
| WO | 2004058762 | 7/2004 |
| WO | 2005004607 | 1/2005 |
| WO | 2006015263 | 2/2006 |
| WO | 2007044796 | 4/2007 |
| WO | 2007064797 | 6/2007 |
| WO | 2007065518 | 6/2007 |
| WO | 2007075567 | 7/2007 |
| WO | 2007130383 | 11/2007 |
| WO | 2007132308 | 11/2007 |
| WO | 2008008539 | 1/2008 |
| WO | 2008075068 | 6/2008 |
| WO | 2009006959 | 1/2009 |
| WO | 2009007074 | 1/2009 |
| WO | 2009050197 | 4/2009 |
| WO | 2009053737 | 4/2009 |
| WO | 2009063061 | 5/2009 |
| WO | 2009080314 | 7/2009 |
| WO | 2009080364 | 7/2009 |
| WO | 2009080533 | 7/2009 |
| WO | 2009080534 | 7/2009 |
| WO | 2009080555 | 7/2009 |
| WO | 2009080721 | 7/2009 |
| WO | 2009080725 | 7/2009 |
| WO | 2009081197 | 7/2009 |
| WO | 2009083076 | 7/2009 |
| WO | 2009083105 | 7/2009 |
| WO | 2009085659 | 7/2009 |
| WO | 2009086041 | 7/2009 |
| WO | 2009086264 | 7/2009 |

OTHER PUBLICATIONS

Berge et al., "Pharmaceutical salts," Journal of Pharmaceutical Science, 1977, vol. 66, No. 1, pp. 1-19.
Berthou, S. et al., "The Met kinase inhibitor SU11274 exhibits a selective inhibition pattern toward different receptor mutated variants," Oncogene, 2004, vol. 23, pp. 5387-5393.
Buchanan, Sean G. "SGX523 is an exquisitely selectively, ATP-competitive inhibitor of the MET receptor tyrosine kinase with antitumor activity in vivo" Molecular Cancer Therapeutics, Dec. 2009;8(12): 3181-3190.
Cancer Drug Design and Discovery, Neidle, Stephen, ed. (Elsevier/Academic Press), pp. 427-431, 2008.
Chen et al., Circulation, 2008, vol. 118, pp. 84-95.
Database Beilstein, Beilstein Institute for Organic Chemistry, Frankfurt, DE, XP002506064, 1991.
Database CA (Online) Chemical Abstracts Service, Columbus, Ohio US:2002, Dushamov, D.A.et al., Acylation of 6-halobenzoxazolin-2-ones by acid chlorides in the presence of a small quantity of iron(III) chloride hexahydrate, XP002496356.
Database CA (Online) Chemical Abstracts Service, Columbus, Ohio US:1979, Domagalina, Eugenia et al, "Acylation of benzoxazolin-2-ones and 3-hydroxyl-1, 2 benzisoxazoles," XP002496357 Polish Journal of Pharmacology and Pharmacy.
Database CA (Online) Chemical Abstracts Service, Columbus, Ohio US; 1967, Nitta, yoshihiro et al: "Benzoxazolone derivatives." XP002496358.
Databse Beilstein, Beilstein Institute for Organic Chemistry, Frankfurt, DE, XP002506065, 2008.
Ettmayer et al. "Lessons Learned from Marketed and Investigational Prodrugs" J. Med. Chem., (2004), 47 (10):2393-2404.
Flouzat, Christine et al. "Synthesis and N-substitution of an uncommon heterocyclic system: oxazolo[5,4-b]pyridin-2(1H)-one," Tetrahedron Letters, Bd, 33, Nr. 32, 1992 Seiten 4571-4574, XP00249354.
Fujisawa Pharmaceut Co Ltd., "Pyrazolopyridine compound and pharmaceutical use thereof," Patent Abstracts of Japan, Publication Date: Jul. 17, 2001; English Abstract of JP-2001 192384.
Glen, H. et al., "E7080, a multi-targeted tyrosin kinase inhibitor suppresses tumor cell migration and invasion," BMC Cancer, 2011, vol. 11, No. 309.
Golub et al. "Molecular Classification of Cancer: Class Discovery and Class Prediction by Gene Expression Monitoring" Science (1999), 286:521-537.
Gould et al., "Salt selection for basic drugs," International Journal of Pharmaceutics, 1986, vol. 33, p. 201.
Guessous, Fadila et al. "An orally Bioavailable c-Met Kinase Inhibitor Potently Inhibits Brain Tumor Malignancy and Growth", Anti-Cancer in Medicinal Chemistry, 2010, 10(1):28-35.
H. Refaat et al., "Synthesis and Anti-Inflammatory Activity of Certain Piperazinylthienylpyridazine Derivatives," Arch Pharm Res., vol. 30, No. 7 (2007) pp. 803-811.
Hackh's Chem Dict., 3rd. Ed., 1944, p. 18.
Hawley's Condensed Chem Dict., 14th Ed., 2002.
Hill, K. S. et al., "Met Receptor Tyrosine Kinase Signaling Induces Secretion of the Angiogenic Chemokine Interleukin-8/CXCL8 in Pancreatic Cancer," PLoS One, Jul. 1, 2012, vol. 7, No. 7, e40420.
http://www.iupac.org/goldbook/A00123.pdf, downloaded Oct. 29, 2010.
Last accessed on Nov. 22, 2011.
International Search Report "International Application No. PCT/EP2008/003696," Date of Completion Sep. 18, 2008, Date of Mailing Oct. 1, 2008, 4 pages.
International Search Report for PCT/EP2008/003473 dated Jul. 28, 2008.
International Search Report for PCT/EP2008/005928 dated Dec. 11, 2008.

(56) References Cited

OTHER PUBLICATIONS

International Search Report of PCT/EP2008/009970 dated Jan. 28, 2009.
International Search Report of PCT/EP2009/002137 (Jun. 4, 2009).
International Search Report of PCT/EP2009/003675 (Aug. 26, 2009).
International Search Report of PCT/EP2009/005172 dated Jan. 26, 2010.
International Search Report of PCT/EP2009/008358 dated Feb. 5, 2010.
Japan Tobacco Inc., "New Amide derivative having vascularization inhibiting action and its use," Patent Abstracts of Japan, Publication Date: Sep. 29, 1998; English Abstracts of JP-10 259176.
Jin et al., Mol. Cancer Ther., Jul. 2006, vol. 5, pp. 1754-1763.
Jin, Hongkui et al. "MetMAb, the One-Armed 5D5 Anti-c-Met Antibody, Inhibits Orthotopic Pancreatic Tumor Growth and Improves Survival", Cancer Res 2008:68(11):4360-4368; Jun. 1, 2008, www.aacrjournals.org.
Johnson et al. "Relationships between drug activity in NCI preclinical in vitro and in vivo models and early clinical trials." British Journal of Cancer (2001) 84(10):1424-1431.
Knowles, Lynn M. et al. "HGF and c-Met Participate in Paracrine Tumorigenic Pathways in Head and Neck Squamous Cell Cancer", Clin Cancer Res, Jun. 1, 2009; 15(11):3740-3750. www.aacrjournals.org.
Lala et al. "Role of nitric oxide in tumor progression: Lessons from experimental tumors." Cancer and Metastasis Review (1998), 17(1), 91-106.
Lima, L. M. et al., "Bioisosterism: a useful strategy for molecular modification and drug design," Current Medicinal Chemistry, 2005, vol. 12, No. 1, pp. 23-49.
Liu, Xiangdong et al. "A novel kinase inhibitor INCB28060 blocks c-MET-dependent signaling, neoplastic activities, and crosstalk with EGFR and HER-3", Clin Cancer Res (45 pages); Published: Sep. 14, 2011.
Locatelli et al., J. Biol. Chem., Jun. 17, 2011, vol. 286, No. 24, pp. 21062-21072.
M. Goekce et al., "Synthesis of New Mannich Bases of Arylpyridazinones as Analgesic and Anti-Inflammatory Agents," Drug Research, vol. 55, No. 6 (2005) pp. 318-325.
Merck Patent GMBH, "New Aryl-alkyl diazinone derivatives," Espacenet, Publication Date: Aug. 14, 1997; English Abstract of DE-196 04 388.
Morissette et al. "High-throughput crystallization: polymorphs, salts, co-crystals and solvates of pharmaceutical solids." Advanced Drug Deliver Reviews 2004, 56 275-300.
Office Action for Related Columbian Patent Application No. 09-138245 dated Sep. 21, 2012.
Qian, Fawn et al. "Inhibition of Tumor Cell Growth, Invasion, and Metastasis by EXEL-2880 (XL880, GSK1363089), a Novel Inhibitor of HGF and VEGF Receptor Tyrosine Kinases", Cancer Res 2009;69(20):8009-8016. Dated: Oct. 15, 2009. www.aacrjournals.org.
Samlowski et al., BJU Int., 2008, vol. 102, No. 2, pp. 162-165, Abstract.
Sampson, Erik R. et al. "The Orally Bioavailable Met Inhibitor PF-2341066 Inhibits Osteosarcoma Growth and Osteolysis/Matrix Production in a Xenograft Model", Journal of Bone and Mineral Research, 26(6):1283-1294; Dated: Jun. 2011.
Sausville et al. "Contributions of Human Tumor Xenografts to Anticancer Drug Development" Cancer Res. 2006, 66(7), Apr. 1, 2006.
Search Report for Chilean Patent Application No. 3854-08 filed Dec. 19, 2008.
Singapore Written Opinion for Application No. 201007486-2 (Sep. 26, 2011).
Smolen et al., Proc. Natl Acad Sci USA, Feb. 2006, vol. 103, No. 7, pp. 2316-2321.
Souillac et al. Characterization of Delivery Systems, Differential Scanning Calorimetry, pp. 217-218 (in Encyclopedia of Controlled Drug Delivery, 1999, John Wiley & Sons.
Stella, V. "Prodrugs as therapeutics" Expert Opin. Ther. Patents (2004), 14(3):277-280.
Testa, B. "Prodrug research: futile or fertile?" Biochemical Pharmacology, 68 (2004): 2097-2106.
Tuynman et al., Br. J. Cancer, 2008, vol. 98, No. 6, pp. 1102-1108, Abstract.
Ucar, Huseyin et al., "Fries Like" Rearragement: a novel and efficient metod for the sythesis of 6-acyl-2(3H)-benzoxazolones and 6-acyl-2(3H)-benzothiazoiones Tetrahedron, Bd.
Underiner et al., Anti-Cancer Agents in Medicinal Chemistry, 2010, vol. 10, pp. 7-27.
Vippagunta, S.R. "Crystalline Solids" Advanced Drug Delivery Reviews 48 (2001):3-26.
Wang et al., Clin Cancer Res., Mar. 15, 2012, vol. 18, No. 6, pp. 1663-1671.
Wolff et al. Burger's Medicinal Chemistry and Drug Discovery. 5th Ed. vol. 1: Principles and Practice, 1995, pp. 975-977.
Ziegler, D. S. et al., "Resistance of human glioblastoma multiforme cells to growth factor inhibitors is overcome by blockade of inhibitors of apoptosis proteins," Journal of.
Zillhardt, Marion et al. Foretinib (GSK1363089), an Orally Available Multikinase Inhibitor of c-Met and VEGFR-2, Blocks Proliferation, Induces Anoikis, and Impairs Ovarian Ca.
Zou, Helen Y. et al. An Orally Available Small-Molecule Inhibitor of c-Met, PF-2341066, Exhibits Cytoreductive Antitumor Efficacy through Antiproliferative and Antiangiogenic.
Zou, Helen Y. et al. "Sensitivity of Selected Human tumor Models to PF-04217903, a Novel Selective c-Met Kinase Inhibitor", Molecular Cancer Therapeutics, American Association.

\* cited by examiner

PYRIMIDINYL-PYRIDAZINONE DERIVATIVES FOR TREATING A DISEASE WHICH IS INFLUENCED BY INHIBITION OF MET KINASE

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases and/or serine/threonine kinases, plays a role, furthermore to pharmaceutical compositions which comprise these compounds, and to the use of the compounds for the treatment of kinase-induced diseases.

In particular, the present invention relates to compounds and to the use of compounds in which the inhibition, regulation and/or modulation of signal transduction by Met kinase plays a role.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

The role of the receptor tyrosine kinase Met in human oncogenesis and the possibility of inhibition of HGF (hepatocyte growth factor) dependent Met activation are described by S. Berthou et al. in Oncogene, Vol. 23, No. 31, pages 5387-5393 (2004). The inhibitor SU11274 described therein, a pyrrole-indoline compound, is potentially suitable for combating cancer. Another Met kinase inhibitor for cancer therapy is described by J. G. Christensen et al. in Cancer Res. 2003, 63(21), 7345-55. A further tyrosine kinase inhibitor for combating cancer is reported by H. Hov et al. in Clinical Cancer Research Vol. 10, 6686-6694 (2004). The compound PHA-665752, an indole derivative, is directed against the HGF receptor c-Met. It is furthermore reported therein that HGF and Met make a considerable contribution to the malignant process of various forms of cancer, such as, for example, multiple myeloma.

The synthesis of small compounds which specifically inhibit, regulate and/or modulate signal transduction by tyrosine kinases and/or serine/threonine kinases, in particular Met kinase, is therefore desirable and an aim of the present invention.

It has been found that the compounds according to the invention and salts thereof have very valuable pharmacological properties while being well tolerated.

The present invention specifically relates to compounds of the formula I which inhibit, regulate and/or modulate signal transduction by Met kinase, to compositions which comprise these compounds, and to processes for the use thereof for the treatment of Met kinase-induced diseases and complaints, such as angiogenesis, cancer, tumour formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases and diseases of the immune system, also autoimmune diseases, cirrhosis, diabetes and diseases of the blood vessels, also instability and permeability and the like in mammals.

Solid tumours, in particular fast-growing tumours, can be treated with Met kinase inhibitors. These solid tumours include monocytic leukaemia, brain, urogenital, lymphatic system, stomach, laryngeal and lung carcinoma, including lung adenocarcinoma and small-cell lung carcinoma.

The present invention is directed to processes for the regulation, modulation or inhibition of Met kinase for the prevention and/or treatment of diseases in connection with unregulated or disturbed Met kinase activity. In particular, the compounds of the formula I can also be employed in the treatment of certain forms of cancer. The compounds of the formula I can furthermore be used to provide additive or synergistic effects in certain existing cancer chemotherapies, and/or can be used to restore the efficacy of certain existing cancer chemotherapies and radiotherapies.

The compounds of the formula I can furthermore be used for the isolation and investigation of the activity or expression of Met kinase. In addition, they are particularly suitable for use in diagnostic methods for diseases in connection with unregulated or disturbed Met kinase activity.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART

Other pyridazine derivatives are described as MET kinase inhibitors in WO 2007/065518.

Thiadiazinones are described in DE19604388, WO2003/037349 WO2007/057093 or WO2007/057092.

Dihydropyridazinones for combating cancer are described in WO 03/037349 A1.

Other pyridazines for the treatment of diseases of the immune system, ischaemic and inflammatory diseases are known from EP 1 043 317 A1 and EP 1 061 077 A1.

EP 0 738 716 A2 and EP 0 711 759 B1 describe other dihydropyridazinones and pyridazinones as fungicides and insecticides.

Other pyridazinones are described as cardiotonic agents in U.S. Pat. No. 4,397,854. JP 57-95964 discloses other pyridazinones.

The use of other MET kinase inhibitors for combating cancer is described in WO 2007/075567.

SUMMARY OF THE INVENTION

The invention relates to compounds selected from the group

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. solvates are, for example, mono- or dihydrates or alkoxides.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds are likewise included. In the case of certain compounds, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound according to the invention and/or tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose.

Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound according to the invention depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or tautomers and stereoisomers thereof, including mixtures thereof in all ratios, and at least one further medicament active ingredient.

The invention also relates to a set (kit) consisting of separate packs of (a) an effective amount of a compound according to the invention and/or tautomers and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound according to the invention and/or tautomers and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds according to the invention and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds according to claim 1 according to the invention for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds according to the invention and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds according to the invention for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds according to the invention can be administered to patients for the treatment of cancer, in particular fast-growing tumours.

The invention thus relates to the use of compounds according to the invention and tautomers and stereoisomers thereof, including mixtures thereof in all ratios, for the preparation of a medicament for the treatment of diseases in which the inhibition, regulation and/or modulation of kinase signal transduction plays a role.

Preference is given here to Met kinase.

Preference is given to the use of compounds according to the invention and tautomers and stereoisomers thereof, including mixtures thereof in all ratios, for the preparation of a medicament for the treatment of diseases which are influenced by inhibition of tyrosine kinases by the compounds according to claim 1.

Particular preference is given to the use for the preparation of a medicament for the treatment of diseases which are influenced by inhibition of Met kinase by the compounds according to the invention according to claim 1.

Especial preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The disclosed compounds according to the invention can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma- Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | | Mitomycin C |

TABLE 1-continued

| Category | Column 2 | Column 3 |
|---|---|---|
| | Plicamycinp | MEN-10755 (Menarini) |
| | Porfiromycin | GPX-100 (Gem Pharmaceuticals) |
| | Cyanomorpholinodoxo-rubicin | |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | |
| | | Azaepothilon B (BMS) |
| | BMS 247550 (BMS) | BNP- 7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT -3 (CollaGenex) |
| | | BMS-275291 (Celltech) |
| Ribonucleoside reductase inhibitors | Marimastat (British Biotech) | Tezacitabine (Aventis) |
| | Gallium maltolate (Titan) | Didox (Molecules for Health) |
| | Triapin (Vion) | |
| TNF-alpha agonists/antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | |
| | GMK (Progenics) | Pentrix (Australian Cancer Technology) |
| | Adenocarcinoma vaccine (Biomira) | |
| | CTP-37 (AVI BioPharma) | JSF-154 (Tragen) |
| | JRX-2 (Immuno-Rx) | Cancer vaccine (Intercell) |
| | PEP-005 (Peplin Biotech) | Norelin (Biostar) |
| | Synchrovax vaccines (CTL Immuno) | BLP-25 (Biomira) |
| | | MGV (Progenics) |
| | | !3-Alethin (Dovetail) |
| | Melanoma vaccine (CTL | CLL-Thera (Vasogen) |

TABLE 1-continued

| | | |
|---|---|---|
| | Immuno) | |
| | p21-RAS vaccine | |
| | (GemVax) | |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol |
| | Tamoxifen | (EntreMed) |
| | Toremofin | Arzoxifen (Eli Lilly) |
| | Dexamethasone | |
| Photodynamic agents | Talaporfin (Light Sciences) | Pd-Bacteriopheophorbid (Yeda) |
| | Theralux (Theratechnologies) | Lutetium-Texaphyrin |
| | Motexafin-Gadolinium | (Pharmacyclics) |
| | (Pharmacyclics) | Hypericin |
| Tyrosine kinase inhibitors | Imatinib (Novartis) | Kahalide F (PharmaMar) |
| | Leflunomide(Sugen/ Pharmacia) | CEP-701 (Cephalon) |
| | | CEP-751 (Cephalon) |
| | ZDI839 (AstraZeneca) | MLN518 (Millenium) |
| | Erlotinib (Oncogene Science) | PKC412 (Novartis) |
| | | Phenoxodiol O |
| | Canertjnib (Pfizer) | Trastuzumab (Genentech) |
| | Squalamine (Genaera) | C225 (ImClone) |
| | SU5416 (Pharmacia) | rhu-Mab (Genentech) |
| | SU6668 (Pharmacia) | MDX-H210 (Medarex) |
| | ZD4190 (AstraZeneca) | 2C4 (Genentech) |
| | ZD6474 (AstraZeneca) | MDX-447 (Medarex) |
| | Vatalanib (Novartis) | ABX-EGF (Abgenix) |
| | PKI166 (Novartis) | IMC-1C11 (ImClone) |
| | GW2016 (GlaxoSmithKline) | |
| | EKB-509 (Wyeth) | |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | |
| | Tiazofurin (IMPDH inhibitor, Ribapharm) | Indisulam (p53 stimulant, Eisai) |
| | Cilengitide (integrin antagonist, Merck KGaA) | Aplidin (PPT inhibitor, PharmaMar) |
| | SR-31747 (IL-1 antagonist, Sanofi-Synthelabo) | Rituximab (CD20 antibody, Genentech) |
| | CCI-779 (mTOR kinase inhibitor, Wyeth) | Gemtuzumab (CD33 antibody, Wyeth Ayerst) |
| | Exisulind (PDE-V inhibitor, Cell Pathways) | PG2 (haematopoiesis promoter, Pharmagenesis) |
| | CP-461 (PDE-V inhibitor, Cell Pathways) | Immunol ™ (triclosan mouthwash, Endo) |
| | AG-2037 (GART inhibitor, | Triacetyluridine (uridine |

TABLE 1-continued

| | | |
|---|---|---|
| | Pfizer) | prodrug, Wellstat) |
| | WX-UK1 (plasminogen activator inhibitor, Wilex) | SN-4071 (sarcoma agent, Signature BioScience) |
| | PBI-1402 (PMN stimulant, ProMetic LifeSciences) | TransMID-107 ™ (immunotoxin, KS Biomedix) |
| | Bortezomib (proteasome inhibitor, Millennium) | PCK-3145 (apoptosis promoter, Procyon) |
| | SRL-172 (T-cell stimulant, SR Pharma) | Doranidazole (apoptosis promoter, Pola) |
| | TLK-286 (glutathione-S transferase inhibitor, Telik) | CHS-828 (cytotoxic agent, Leo) |
| | PT-100 (growth factor agonist, Point Therapeutics) | Trans-retinic acid (differentiator, NIH) |
| | Midostaurin (PKC inhibitor, Novartis) | MX6 (apoptosis promoter, MAXIA) |
| | Bryostatin-1 (PKC stimulant, GPC Biotech) | Apomine (apoptosis promoter, ILEX Oncology) |
| | CDA-II (apoptosis promoter, Everlife) | Urocidin (apoptosis promoter, Bioniche) |
| | SDX-101 (apoptosis promoter, Salmedix) | Ro-31-7453 (apoptosis promoter, La Roche) |
| | Ceflatonin (apoptosis promoter, ChemGenex) | Brostallicin (apoptosis promoter, Pharmacia) |
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | |
| | Teniposide or mitoxantrone | Quinamed (ChemGenex) |
| | | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | | BNP-1350 (BioNumerik) |
| | Pixantrone (Novuspharma) | CKD-602 (Chong Kun Dang) |
| | Rebeccamycin analogue (Exelixis) | KW-2170 (Kyowa Hakko) |
| | BBR-3576 (Novuspharma) | |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |

TABLE 1-continued

| Category | Drug | Drug |
|---|---|---|
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxo-rubicin | |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | |
| | Vincristine | IDN 5109 (Bayer) |
| | Vinorelbine | A 105972 (Abbott) |
| | Vindesine | A 204197 (Abbott) |
| | Dolastatin 10 (NCI) | LU 223651 (BASF) |
| | Rhizoxin (Fujisawa) | D 24851 (ASTA Medica) |
| | Mivobulin (Warner-Lambert) | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP- 7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-Benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT -3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immuno-modulators | Interferon | Dexosome therapy (Anosys) |
| | Oncophage (Antigenics) | |
| | GMK (Progenics) | Pentrix (Australian Cancer Technology) |
| | Adenocarcinoma vaccine (Biomira) | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | | !3-Alethin (Dovetail) |

TABLE 1-continued

| | | |
|---|---|---|
| | Melanoma vaccine (CTL Immuno) | CLL-Thera (Vasogen) |
| | p21-RAS vaccine (GemVax) | |
| Hormonal and antihormonal agents | Oestrogens | Prednisone |
| | Conjugated oestrogens | Methylprednisolone |
| | Ethynyloestradiol chlorotrianisene | Prednisolone Aminoglutethimide |
| | Idenestrol | Leuprolide |
| | Hydroxyprogesterone caproate | Goserelin Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (EntreMed) |
| | Tamoxifen | |
| | Toremofin | Arzoxifen (Eli Lilly) |
| | Dexamethasone | |
| Photodynamic agents | Talaporfin (Light Sciences) | Pd-Bacteriopheophorbid (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide(Sugen/ Pharmacia) | CEP-701 (Cephalon) CEP-751 (Cephalon) |
| | ZDI839 (AstraZeneca) | MLN518 (Millenium) |
| | Erlotinib (Oncogene Science) | PKC412 (Novartis) Phenoxodiol O |
| | Canertjnib (Pfizer) | Trastuzumab (Genentech) |
| | Squalamine (Genaera) | C225 (ImClone) |
| | SU5416 (Pharmacia) | rhu-Mab (Genentech) |
| | SU6668 (Pharmacia) | MDX-H210 (Medarex) |
| | ZD4190 (AstraZeneca) | 2C4 (Genentech) |
| | ZD6474 (AstraZeneca) | MDX-447 (Medarex) |
| | Vatalanib (Novartis) | ABX-EGF (Abgenix) |
| | PKI166 (Novartis) | IMC-1C11 (ImClone) |
| | GW2016 (GlaxoSmithKline) | |
| | EKB-509 (Wyeth) | |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | |
| | Cilengitide (integrin antagonist, Merck KGaA) | Aplidin (PPT inhibitor, PharmaMar) |
| | SR-31747 (IL-1 antagonist, Sanofi-Synthelabo) | Rituximab (CD20 antibody, Genentech) |
| | CCI-779 (mTOR kinase inhibitor, Wyeth) | Gemtuzumab (CD33 antibody, Wyeth Ayerst) |
| | Exisulind (PDE-V inhibitor, Cell Pathways) | PG2 (haematopoiesis promoter, Pharmagenesis) |
| | CP-461 (PDE-V inhibitor, Cell Pathways) | Immunol ™ (triclosan mouthwash, Endo) |

TABLE 1-continued

| | |
|---|---|
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | Trans-retinic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

A combined treatment of this type can be achieved with the aid of simultaneous, consecutive or separate dispensing of the individual components of the treatment. Combination products of this type employ the compounds according to the invention.

ASSAYS

The compounds of the formula I described in the examples were tested by the assays described below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Measurement of Met Kinase Activity

According to the manufacturer's data (Met, active, upstate, catalogue No. 14-526), Met kinase is expressed for the purposes of protein production in insect cells (Sf21; S. frugiperda) and subsequent affinity-chromatographic purification as "N-terminal 6His-tagged" recombinant human protein in a baculovirus expression vector.

The kinase activity can be measured using various available measurement systems. In the scintillation proximity method (Sorg et al., J. of Biomolecular Screening, 2002, 7, 11-19), the flashplate method or the filter binding test, the radioactive phosphorylation of a protein or peptide as substrate is measured using radioactively labelled ATP ($^{32}$P-ATP, $^{33}$P-ATP). In the case of the presence of an inhibitory compound, a reduced radioactive signal, or none at all, can be detected. Furthermore, homogeneous time-resolved fluorescence resonance energy transfer (HTR-FRET) and fluoroescence polarisation (FP) technologies can be used as assay methods (Sills et al., J. of Biomolecular Screening, 2002, 191-214).

Other non-radioactive ELISA assay methods use specific phospho-antibodies (phospho-ABs). The phospho-antibody only binds the phosphorylated substrate. This binding can be detected by chemiluminescence using a second peroxidase-conjugated antibody (Ross et al., 2002, Biochem. J.).

Flashplate Method (Met Kinase)

The test plates used are 96-well Flashplate® microtitre plates from Perkin Elmer (Cat. No. SMP200). The components of the kinase reaction described below are pipetted into the assay plate. The Met kinase and the substrate poly Ala-Glu-Lys-Tyr, (pAGLT, 6:2:5:1), are incubated for 3 hrs at room temperature with radioactively labelled $^{33}$P-ATP in the presence and absence of test substances in a total volume of 100 µl. The reaction is terminated using 150 µl of a 60 mM EDTA solution. After incubation for a further 30 min at room temperature, the supernatants are filtered off with suction, and the wells are washed three times with 200 µl of 0.9% NaCl solution each time. The measurement of the bound radioactivity is carried out by means of a scintillation measuring instrument (Topcount NXT, Perkin-Elmer).

The full value used is the inhibitor-free kinase reaction. This should be approximately in the range 6000-9000 cpm. The pharmacological zero value used is staurosporin in a final concentration of 0.1 mM. The inhibitory values (IC50) are determined using the RS1_MTS program.

Kinase reaction conditions per well:
30 µl of assay buffer
10 µl of substance to be tested in assay buffer with 10% of DMSO
10 µl of ATP (final concentration 1 µM cold, 0.35 µCi of $^{33}$P-ATP)
50 µl of Met kinase/substrate mixture in assay buffer;
    (10 ng of enzyme/well, 50 ng of pAGLT/well)
  Solutions used:
    Assay buffer:
  50 mM HEPES
    3 mM magnesium chloride
    3 µM sodium orthovanadate
    3 mM manganese(II) chloride
    1 mM dithiothreitol (DTT)
  pH = 7.5 (to be set using sodium hydroxide)
    Stop solution:
  60 mM Titriplex III (EDTA)
    $^{33}$P-ATP: Perkin-Elmer;
    Met kinase: Upstate, Cat. No. 14-526, Stock 1 µg/10 µl; spec. activity 954 U/mg;
  Poly-Ala-Glu-Lys-Tyr, 6:2:5:1: Sigma Cat. No. P1152

In-Vivo Tests (Figure. 1/1)

Experimental Procedure: Female Balb/C mice (breeder: Charles River Wiga) were 5 weeks old on arrival. They were acclimatised to our keeping conditions for 7 days. Each mouse was subsequently injected subcutaneously in the pelvic area with 4 million TPR-Met/NIH3T3 cells in 100 µl of PBS (without Ca++ and Mg++). After 5 days, the animals were randomised into 3 groups, so that each group of 9 mice had an average tumour volume of 110 µl (range: 55-165). 100 µl of vehicle (0.25% methylcellulose/100 mM acetate buffer, pH 5.5) were administered daily to the control group, and 200 mg/kg of "A56" or "A91" dissolved in the vehicle (volume likewise 100 µl/animal) were administered daily to the treatment groups, in each case by gastric tube. After 9 days, the controls had an average volume of 1530 µl and the experiment was terminated.

Measurement of the Tumour Volume: The length (L) and breadth (B) were measured using a Vernier calliper, and the tumour volume was calculated from the formula L×B×B/2.

Keeping Conditions: 4 or 5 animals per cage, feeding with commercial mouse food (Sniff).

The compounds "A18" and "A22" have a significant antitumoural action.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

Mass spectrometry (MS): EI (electron impact ionisation) M+
FAB (fast atom bombardment) (M+H)+
ESI (electrospray ionisation) (M+H)+
APCI-MS (atmospheric pressure chemical ionisation-mass spectrometry) (M+H)+.
Mass spectrometry (MS): EI (electron impact ionisation) M+
FAB (fast atom bombardment) (M+H)+
ESI (electrospray ionisation) (M+H)+
APCI-MS (atmospheric pressure chemical ionisation-mass spectrometry) (M+H)+.
HPLC/MS Analyses
are carried out in a 3µ Silica-Rod column with a 210 second gradient from 20 to 100% water/acetonitrile/0.01% of trifluoroacetic acid, at a flow rate of 2.2 ml/min, and detection at 220 nm.
HPLC Analyses (Method A)
Column: Chromolith RP18e 100*3 mm
Flow rate: 2 ml/min
Solvent A: H₂O+0.1% of trifluoroacetic acid
Solvent B: acetonitrile+0.1% of trifluoroacetic acid
Gradient 5 min
0-4 min: 99:1->1:99
4-5 min: 1:99-1:99
HPLC Analyses (Method B)
Column: Chromolith RP18e 100*3 mm
Flow rate: 4 ml/min
Solvent A: H₂O+0.05% of HCOOH
Solvent B: acetonitrile+10% of solvent A
Gradient 8 min
0-1 min: 99:1->99:1
1-7 min: 99:1-1:99
7-8 min: 1:99->1:99
HPLC Analysis (Method C)
Flow rate: 2 ml/min
99:01-0:100 water+0.1% (vol.) of TFA:acetonitrile+0.1% (vol.) of TFA
0.0 to 0.2 min: 99:01
0.2 to 3.8 min: 99:01-->0:100
3.8 to 4.2 min: 0:100
Column: Chromolith Performance RP18e; 100 mm long, internal diameter 3 mm, wavelength: 220 nm
Retention time Rt in minutes [min].

EXAMPLE 1 (COMPARATIVE EXAMPLE)

The preparation of the compounds
6-(1-methyl-1H-pyrazol-4-yl)-2-{3-[5-(2-morpholin-4-ylethoxy)pyrimidin-2-yl]-benzyl}-2H-pyridazin-3-one ("A229"),
2-[3-(5-bromopyrimidin-2-yl)benzyl]-6-(1-methyl-1H-pyrazol-4-yl)-2H-pyridazin-3-one ("A230") and
2-[3-(5-hydroxypyrimidin-2-yl)benzyl]-6-(1-methyl-1H-pyrazol-4-yl)-2H-pyridazin-3-one ("A231")
is carried out analogously to the following scheme

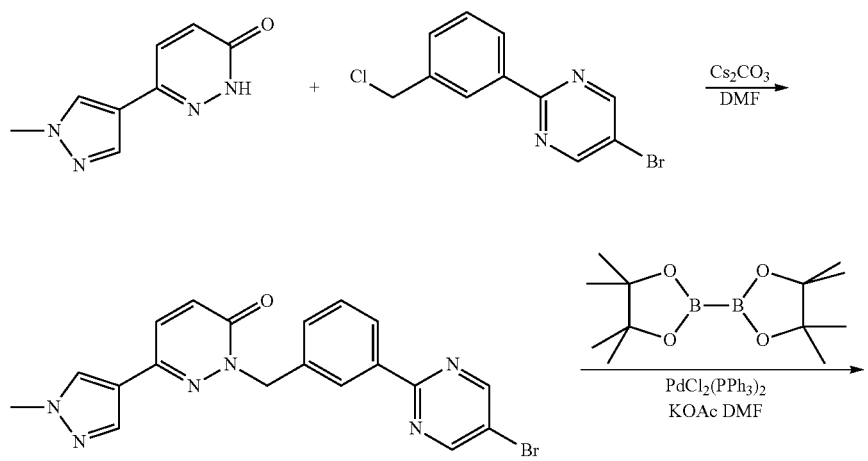

"A230"

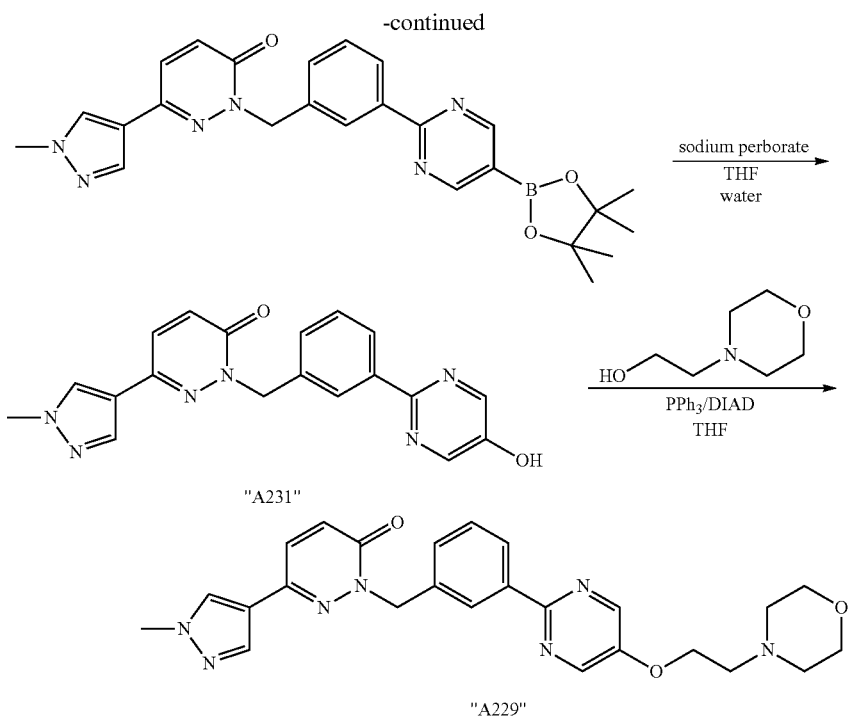

"A231"

"A229"

12.4 g (43.6 mmol) of 5-bromo-2-(3-chloromethylphenyl) pyrimidine and 14.2 g (43.6 mmol) of caesium carbonate are added to a suspension of 7.68 g (43.6 mmol) of 6-(1-methyl-1H-pyrazol-4-yl)-2H-pyridazin-3-one in 90 ml of DMF, and the mixture is stirred at room temperature for 24 hours. The reaction mixture is added to 400 ml of water. The resultant precipitate is filtered off with suction, washed with water and dried in vacuo; 2-[3-(5-bromopyrimidin-2-yl)benzyl]-6-(1-methyl-1H-pyrazol-4-yl)-2H-pyridazin-3-one as yellow-brown crystals; m.p. 184° C.; ESI 423, 425.

10.9 g (42.9 g) of bis(pinacolato)diboron and 9.72 g (99.0 mmol) of potassium acetate are added to a suspension of 14.0 g (33.0 mmol) of 2-[3-(5-bromopyrimidin-2-yl)benzyl]-6-(1-methyl-1H-pyrazol-4-yl)-2H-pyridazin-3-one in 65 ml of DMF, and the mixture is heated to 70° C. under nitrogen. After stirring for 15 minutes at this temperature, 695 mg (0.99 mmol) of bis(triphenylphosphine)palladium(II) chloride are added, and the reaction mixture is stirred at 70° C. under nitrogen for 18 hours. The reaction mixture is allowed to cool to room temperature, water and dichloromethane are added, the mixture is filtered through kieselguhr, and the organic phase is separated off. The organic phase is dried over sodium sulfate, evaporated, and the residue is recrystallised from 2-propanol: 6-(1-methyl-1H-pyrazol-4-yl)-2-{3-[5-(4,4,5,5-tetramethyl-1,3,2-dioxaborolan-2-yl)pyrimidin-2-yl]benzyl}-2H-pyridazin-3-one as grey crystals; m.p. 204° C.;

$^1$H-NMR (d$_6$-DMSO): δ [ppm]=1.34 (s, 12H), 3.87 (s, 3H), 5.35 (s, 2H), 7.05 (d, J=9.6 Hz, 1H), 7.52 (m, 2H), 7.80 (d, J=9.6 Hz, 1H), 7.89 (s, 1H), 8.21 (s, 1H), 8.35 (m, 1H), 8.45 (bs, 1H), 9.01 (s, 2H).

8.50 g (85.1 mmol) of sodium perborate are added in portions with ice-cooling to a suspension of 13.4 g (28.4 mmol) of 6-(1-methyl-1H-pyrazol-4-yl)-2-{3-[5-(4,4,5,5-tetramethyl-1,3,2-dioxaborolan-2-yl)pyrimidin-2-yl]benzyl}-2H-pyridazin-3-one in 55 ml of THF and 55 ml of water, and the mixture is stirred at room temperature for 2 hours. The reaction mixture is filtered through kiesel-Buhr with suction. The filtrate is concentrated to about half the original volume in vacuo and adjusted to a pH of 1 using 2 N hydrochloric acid. The resultant precipitate is filtered off with suction, washed with water and dried in vacuo: 2-[3-(5-hydroxypyrimidin-2-yl)benzyl]-6-(1-methyl-1H-pyrazol-4-yl)-2H-pyridazin-3-one as pale-beige crystals; m.p. 239° C.; ESI 361.

394 mg (1.50 mmol) of triphenylphosphine and 242 μl (2.00 mmol) of 4-(2-hydroxyethyl)morpholine are added successively to a suspension of 360 mg (1.00 mmol) of 2-[3-(5-hydroxypyrimidin-2-yl)benzyl]-6-(1-methyl-1H-pyrazol-4-yl)-2H-pyridazin-3-one in 2 ml of THF. 294 μl (1.50 mmol) of diisopropyl azodicarboxylate are then slowly added dropwise with ice-cooling. The resultant solution is stirred at room temperature for 18 hours. The reaction mixture is evaporated in vacuo, and the oily residue is dissolved in 2-propanol. The solid which forms after some time is filtered off with suction, washed with 2-propanol and tert-butyl methyl ether and dried in vacuo: 6-(1-methyl-1H-pyrazol-4-yl)-2-{3-[5-(2-morpholin-4-ylethoxy)pyrimidin-2-yl]benzyl}-2H-pyridazin-3-one ("A229") as colourless crystals; m.p. 134° C.; ESI 474;

$^1$H-NMR (d$_6$-DMSO): δ [ppm]=2.48 (m, 4H), 2.73 (t, J=5.5 Hz, 2H), 3.57 (m, 4H), 3.87 (s, 3H), 4.30 (t, J=5.5 Hz, 2H), 5.33 (s, 2H), 7.05 (d, J=9.5 Hz, 1H), 7.43 (dt, J$_1$=7.3 Hz, J$_2$=1.5 Hz, 1H), 7.47 (t, J=7.5 Hz, 1H), 7.80 (d, J=9.5 Hz, 1H), 7.89 (s, 1H), 8.21 (s, 1H), 8.22 (dt, J$_1$=7.5 Hz, J$_2$=1.5 Hz, 1H), 8.28 (bs, 1H), 8.64 (s, 2H).

Salt formation from "A229" gives the p-toluenesulfonate and the phosphate.

The following compounds are obtained analogously under standard conditions

| Compound No. | Name and/or structure | ESI [M + H]+ |
|---|---|---|
| "A232" | 6-(1-Methyl-1H-pyrazol-4-yl)-2-{3-[5-(2-morpholin-4-yl-ethoxy)pyrimidin-2-yl]benzyl}-2H-pyridazin-3-one, hydrochloride (from "A229") | 474 |
| "A236" | 6-(1-Methyl-1H-pyrazol-4-yl)-2-{3-[5-(2-morpholin-4-yl-ethoxy)pyrimidin-2-yl]benzyl}-2H-pyridazin-3-one, dihydrochloride (from "A229") | 474 |

EXAMPLE 2

The following compounds are obtained analogously to Example 1 under standard conditions

| "A1" | 6-(1-Methyl-1H-pyrazol-4-yl)-2-{3-[5-(2-morpholin-4-yl-ethoxy)pyrimidin-2-yl]benzyl}-2H-pyridazin-3-one, sulfate |
|---|---|
| "A2" | 6-(1-Methyl-1H-pyrazol-4-yl)-2-{3-[5-(2-morpholin-4-yl-ethoxy)pyrimidin-2-yl]benzyl}-2H-pyridazin-3-one, mesylate |
| "A3" | 6-(1-Methyl-1H-pyrazol-4-yl)-2-{3-[5-(2-morpholin-4-yl-ethoxy)pyrimidin-2-yl]benzyl}-2H-pyridazin-3-one, besylate |
| "A4" | 6-(1-Methyl-1H-pyrazol-4-yl)-2-{3-[5-(2-morpholin-4-yl-ethoxy)pyrimidin-2-yl]benzyl}-2H-pyridazin-3-one, p-tosylate |
| "A5" | 6-(1-Methyl-1H-pyrazol-4-yl)-2-{3-[5-(2-morpholin-4-yl-ethoxy)pyrimidin-2-yl]benzyl}-2H-pyridazin-3-one, fumarate |
| "A6" | 6-(1-Methyl-1H-pyrazol-4-yl)-2-{3-[5-(2-morpholin-4-yl-ethoxy)pyrimidin-2-yl]benzyl}-2H-pyridazin-3-one, maleate |

EXAMPLE 3 (COMPARATIVE EXAMPLE)

The preparation of the compound 3-(1-{3-[5-(1-methylpiperidin-4-ylmethoxy)pyrimidin-2-yl]benzyl}-6-oxo-1,6-dihydropyridazin-3-yl)benzonitrile ("A257") is carried out analogously to the following scheme

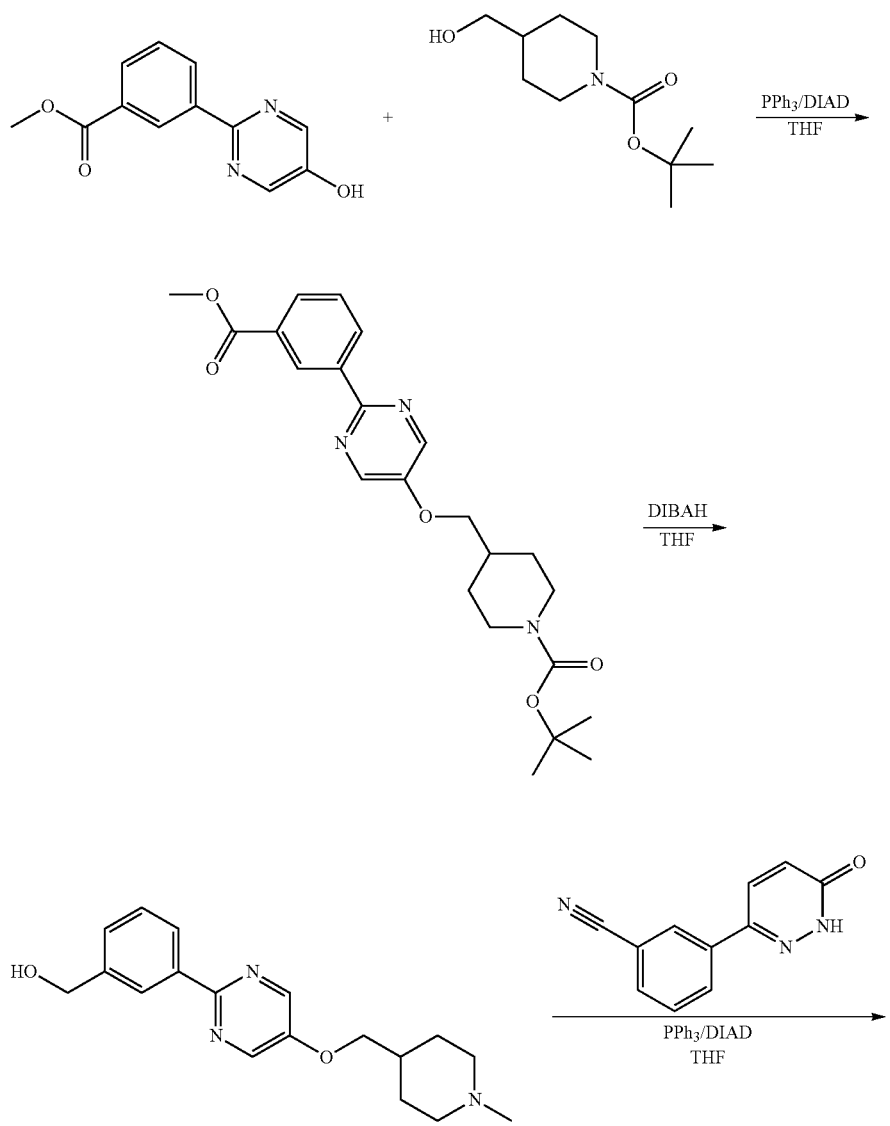

-continued

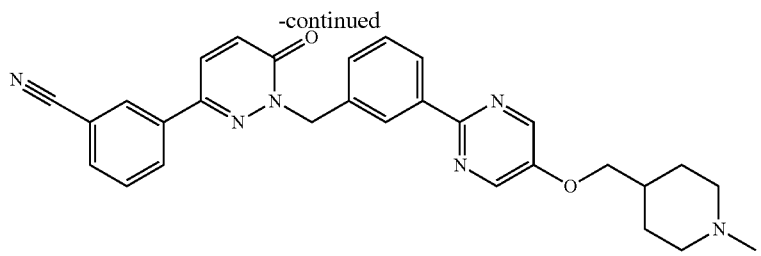

"A257"

17.7 g (67.8 mmol) of triphenylphosphine are added to a suspension of 13.0 g (56.5 mmol) of methyl 3-(5-hydroxypyrimidin-2-yl)benzoate and 13.4 g (62.1 mmol) of N-Boc-piperidinylmethanol in 115 ml of THF, and the mixture is cooled to 5° C. 13.3 ml (67.8 mmol) of diisopropyl azodicarboxylate are added dropwise to the suspension held at this temperature over the course of 45 minutes with stirring. The reaction mixture is stirred at room temperature for 1 hour. A further 22.2 g (84.7 mmol) of triphenylphosphine and 16.6 ml (84.7 mmol) of diisopropyl azodicarboxylate are subsequently added. The reaction mixture is stirred at room temperature for 18 hours and evaporated in vacuo. The resultant solid is filtered off with suction, washed with diethyl ether and chromatographed on a silica-gel column with dichloromethane/methanol as eluent: tert-butyl 4-[2-(3-methoxycarbonylphenyl)pyrimidin-5-yloxymethyl]-piperidine-1-carboxylate as lemon-yellow crystals; m.p. 166° C.; ESI 428.

25 ml (25 mmol) of a 1 M solution of diisobutylaluminium hydride in THF are added dropwise under nitrogen to a suspension of 1.71 g (3.99 mmol) of tertbutyl 4-[2-(3-methoxycarbonylphenyl)pyrimidin-5-yloxymethyl]piperidine-1-carboxylate in 20 ml of THF. The reaction mixture is stirred at room temperature for 1 hour, and 1 ml of a saturated sodium sulfate solution is added. The resultant precipitate is filtered off with suction and washed with THF and hot 2-propanol. The filtrate is evaporated and recrystallised from tert-butyl methyl ether: {3-[5-(1-methylpiperidin-4-ylmethoxy)pyrimidin-2-yl]phenyl}methanol as beige crystals; m.p. 175° C.; ESI 314.

264 mg (1.30 mmol) of 3-(6-oxo-1,6-dihydropyridazin-3-yl)benzonitrile and 397 mg (1.5 mmol) of triphenylphosphine are added successively to a solution of 313 mg (1.00 mmol) of {3-[5-(1-methylpiperidin-4-ylmethoxy)pyrimidin-2-yl]-phenyl}methanol in 2 ml of THF. The reaction mixture is cooled in an ice bath, and 294 µl (1.5 mmol) of diisopropyl azodicarboxylate are added dropwise with stirring. The reaction mixture is stirred at room temperature for 18 hours and evaporated. The residue is chromatographed on a silica-gel column with dichloromethane/methanol. The product-containing fractions are combined, evaporated, the residue is digested with tert-butyl methyl ether, filtered off with suction and dried in vacuo: 3-(1-{3-[5-(1-methylpiperidin-4-ylmethoxy)pyrimidin-2-yl]benzyl}-6-oxo-1,6-dihydropyridazin-3-yl)benzonitrile as colourless crystals; m.p. 177° C.; ESI 493;

$^1$H-NMR (d$_6$-DMSO): δ [ppm]=1.33 (m, 2H), 1.75 (m, 3H), 1.89 (m, 2H), 2.17 (s, 3H), 2.80 (m, 2H), 4.05 (d, J=6.1 Hz, 2H), 5.45 (s, 2H), 7.16 (d, J=10 Hz, 1H), 7.49 (m, 2H), 7.73 (t, J=7.8 Hz, 1H), 7.93 (d, J=7.8 Hz, 1H), 8.17 (d, J=10 Hz, 1H), 8.24 (m, 2H), 8.38 (m, 2H), 8.64 (s, 2H).

Salt formation from "A257" gives the hemisulfate, citrate, tartrate, sulfate, succinate and hydrochloride.

EXAMPLE 4

The following compounds are obtained analogously to Example 3 under standard conditions

| Compound No. | Name and/or structure | ESI [M + H]$^+$ |
|---|---|---|
| "A7" | 2.233 ml of 1N hydrochloric acid are added to 1 g of "A257" in 150 ml of acetone, giving a clear solution. The solution is filtered, stirred at room temperature for 16 h, and the precipitated product 3-(1-{3-[5-(1-methyl-piperidin-4-ylmethoxy)pyrimidin-2-yl]benzyl}-6-oxo-1,6-dihydropyridazin-3-yl)benzonitrile, hydrochloride monohydrate ("A7") is separated off. | |
| | $^1$H NMR (400 MHz, DMSO-d$_6$) δ [ppm] 10.374 (sb, 1H), 8.658 (s, 2H), 8.381 (m, 2H), 8.243 (m, 2H), 8.175 (d, 1H), 7.932 (d, 1H), 7.723 (t, 1H), 7.495 (m, 2H), 7.163 (d, 1H), 5.452 (s, 2H), 4.095 (d, 1H), 3.440 (m, 2H), 2.723 (s, 3H), 2.058 (m, 1H), 1.982 (m, 2H), 1.613 (m, 2H); | |
| | Elemental analysis: | |
| | Actual / Nominal | |
| | C = 63.6% / C = 63.7% | |
| | H = 5.6% / H = 5.7% | |
| | N = 15.2% / N = 15.4% | |
| | O = 8.9% / O = 8.8% | |
| | Cl = 6.0% / Cl = 6.5% | |
| "A8" | 3-(1-{3-[5-(1-Methylpiperidin-4-ylmethoxy)pyrimidin-2-yl]-benzyl}-6-oxo-1,6-dihydropyridazin-3-yl)benzonitrile, hydrobromide | |

-continued

| Compound No. | Name and/or structure | ESI [M + H]$^+$ |
|---|---|---|
| "A9" | 3-(1-{3-[5-(1-Methylpiperidin-4-ylmethoxy)pyrimidin-2-yl]-benzyl}-6-oxo-1,6-dihydropyridazin-3-yl)benzonitrile, mesylate | |

$^1$H NMR (400 MHz, DMSO-d$_6$) δ [ppm] 9.309 (sb, 1H), 8.654 (s, 2H), 8.380 (m, 2H), 8.246 (m, 2H), 8.174 (d, 1H), 7.929 (d, 1H), 7.720 (t, 1H), 7.493 (m, 2H), 7.160 (d, 1H), 5.449 (s, 2H), 4.102 (d, 2H), 3.482 (m, 2H), 2.993 (m, 2H), 2.783 (s, 3H), 2.352 (s, 3H), 1.973 (m, 3H), 1.551 (m, 2H)

| | | |
|---|---|---|
| "A10" | 3-(1-{3-[5-(1-Methylpiperidin-4-ylmethoxy)pyrimidin-2-yl]-benzyl}-6-oxo-1,6-dihydropyridazin-3-yl)benzonitrile, besylate | |
| "A11" | 3-(1-{3-[5-(1-Methylpiperidin-4-ylmethoxy)pyrimidin-2-yl]-benzyl}-6-oxo-1,6-dihydropyridazin-3-yl)benzonitrile, malate | |

$^1$H NMR (400 MHz, DMSO-d$_6$) δ [ppm] 8.654 (s, 2H), 8.375 (m, 2H), 8.237 (m, 2H), 8.167 (d, 1H), 7.927 (d, 1H), 7.719 (t, 1H), 7.491 (m, 2H), 7.157 (d, 1H), 5.447 (s, 2H), 4.087 (d, 2H), 3.977 (m, 2H), 3.195 (d, 2H), 2.585 (m, 2H), 2.545 (s, 3H), 2.356 (m, 1H), 1.947 (m, 1H), 1.896 (m, 2H), 1.466 (m, 2H)

| | | |
|---|---|---|
| "A12" | 3-(1-{3-[5-(1-Methylpiperidin-4-ylmethoxy)pyrimidin-2-yl]-benzyl}-6-oxo-1,6-dihydropyridazin-3-yl)benzonitrile, fumarate | |

$^1$H NMR (400 MHz, DMSO-d$_6$) δ [ppm] 8.654 (s, 2H), 8.377 (m, 2H), 8.218-8.250 (m, 2H), 8.167 (d, 1H), 7.926 (d, 1H), 7.716 (t, 1H), 7.476-7.489 (m, 2H), 7.156 (d, 1H), 6.546 (s, 2H), 5.445 (s, 2H), 4.062 (d, 2H), 3.019 (d, 2H), 2.365 (s, 3H), 2.273 (t, 2H), 1.807-1.890 (m, 3H), 1.386-1.462 (m, 2H)

| | | |
|---|---|---|
| "A13" | 3-(1-{3-[5-(1-Methylpiperidin-4-ylmethoxy)pyrimidin-2-yl]-benzyl}-6-oxo-1,6-dihydropyridazin-3-yl)benzonitrile, maleate | |

$^1$H NMR (400 MHz, DMSO-d$_6$) δ [ppm] 9.451 (sb, 1H), 8.655 (s, 2H), 8.379 (m, 2H), 8.248 (m, 2H), 8.170 (d, 1H), 7.930 (d, 1H), 7.719 (t, 1H), 7.493 (m, 2H), 7.160 (d, 1H), 6.032 (S), 5.450 (s, 2H), 4.120 (d, 2H), 3.442 (m, 2H), 2.990 (m, 2H), 2.764 (s, 3H), 2.026 (m, 3H), 1.571 (m, 2H)

| | | |
|---|---|---|
| "A14" | 3-(1-{3-[5-(1-Methylpiperidin-4-ylmethoxy)pyrimidin-2-yl]-benzyl}-6-oxo-1,6-dihydropyridazin-3-yl)benzonitrile, p-tosylate | |

$^1$H NMR (400 MHz, DMSO-d$_6$) δ 9.117 (sb, 1H), 8.651 (s, 2H), 8.375 (m, 2H), 8.240 (m, 2H), 8.171 (d, 1H), 7.929 (d, 1H), 7.719 (t, 1H), 7.486 (m, 4H), 7.158 (d, 1H), 7.109 (d, 2H), 5.448 (s, 2H), 4.106 (sb, 1H), 3.460 (sb, 2H), 2.772 (s, 3H), 2.284 (s, 3H), 1.998 (m, 3H), 1.513 (m, 2H)

Pharmacological Data

TABLE 1

Met kinase inhibition of some compounds according to the invention

| Compound No. | IC$_{50}$ (cell assay) | IC$_{50}$ (enzyme assay) |
|---|---|---|
| "A1" | <100 nM | <100 nM |
| "A2" | <100 nM | <100 nM |
| "A3" | <100 nM | <100 nM |
| "A4" | <100 nM | <100 nM |
| "A5" | <100 nM | <100 nM |
| "A6" | <100 nM | <100 nM |
| "A7" | <100 nM | <100 nM |
| "A8" | <100 nM | <100 nM |
| "A9" | <100 nM | <100 nM |
| "A10" | <100 nM | <100 nM |
| "A11" | <100 nM | <100 nM |
| "A12" | <100 nM | <100 nM |
| "A13" | <100 nM | <100 nM |
| "A14" | <100 nM | <100 nM |

The following examples relate to medicaments:

EXAMPLE A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C: Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D: Ointment 500 mg of an active ingredient of the formula I are mixed with 99.5 g of Vaseline under aseptic conditions.

EXAMPLE E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F: Dragees

Tablets are pressed analogously to Example E and subsequently coated in a conventional manner with a coating of sucrose, potato starch, talc, tragacanth and dye.

EXAMPLE G: Capsules 2 kg of active ingredient of the formula I are introduced into hard gelatine capsules in a conventional manner in such a way that each capsule contains 20 mg of the active ingredient.

EXAMPLE H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A method for treating a disease which is influenced by inhibition of Met kinase, wherein treating does not include prevention, or a method for stabilizing or improving the clinical symptoms of a disease which is influenced by inhibition of Met kinase,
comprising administering to a subject having said disease a pharmaceutical composition,
comprising
a pharmaceutically acceptable carrier, and
an active ingredient selected from the group consisting of

| No. | Name |
|---|---|
| "A1" | 6-(1-Methyl-1H-pyrazol-4-yl)-2-{3-[5-(2-morpholin-4-ylethoxy)pyrimidin-2-yl]-benzyl}-2H-pyridazin-3-one, sulfate |
| "A2" | 6-(1-Methyl-1H-pyrazol-4-yl)-2-{3-[5-(2-morpholin-4-ylethoxy)pyrimidin-2-yl]-benzyl}-2H-pyridazin-3-one, mesylate |
| "A3" | 6-(1-Methyl-1H-pyrazol-4-yl)-2-{3-[5-(2-morpholin-4-ylethoxy)pyrimidin-2-yl]-benzyl}-2H-pyridazin-3-one, besylate |
| "A4" | 6-(1-Methyl-1H-pyrazol-4-yl)-2-{3-[5-(2-morpholin-4-ylethoxy)pyrimidin-2-yl]-benzyl}-2H-pyridazin-3-one, p-tosylate |
| "A5" | 6-(1-Methyl-1H-pyrazol-4-yl)-2-{3-[5-(2-morpholin-4-ylethoxy)pyrimidin-2-yl]-benzyl}-2H-pyridazin-3-one, fumarate |
| "A6" | 6-(1-Methyl-1H-pyrazol-4-yl)-2-{3-[5-(2-morpholin-4-ylethoxy)pyrimidin-2-yl]-benzyl}-2H-pyridazin-3-one, maleate |
| "A7" | 3-(1-{3-[5-(1-Methylpiperidin-4-ylmethoxy)pyrimidin-2-yl]benzyl}-6-oxo-1,6-dihydropyridazin-3-yl)benzonitrile, hydrochloride monohydrate |
| "A8" | 3-(1-{3-[5-(1-Methylpiperidin-4-ylmethoxy)pyrimidin-2-yl]benzyl}-6-oxo-1,6-dihydropyridazin-3-yl)benzonitrile, hydrobromide |
| "A9" | 3-(1-{3-[5-(1-Methylpiperidin-4-ylmethoxy)pyrimidin-2-yl]benzyl}-6-oxo-1,6-dihydropyridazin-3-yl)benzonitrile, mesylate |
| "A10" | 3-(1-{3-[5-(1-Methylpiperidin-4-ylmethoxy)pyrimidin-2-yl]benzyl}-6-oxo-1,6-dihydropyridazin-3-yl)benzonitrile, besylate |
| "A11" | 3-(1-{3-[5-(1-Methylpiperidin-4-ylmethoxy)pyrimidin-2-yl]benzyl}-6-oxo-1,6-dihydropyridazin-3-yl)benzonitrile, malate |
| "A12" | 3-(1-{3-[5-(1-Methylpiperidin-4-ylmethoxy)pyrimidin-2-yl]benzyl}-6-oxo-1,6-dihydropyridazin-3-yl)benzonitrile, fumarate |
| "A13" | 3-(1-{3-[5-(1-Methylpiperidin-4-ylmethoxy)pyrimidin-2-yl]benzyl}-6-oxo-1,6-dihydropyridazin-3-yl)benzonitrile, maleate, and |
| "A14" | 3-(1-{3-[5-(1-Methylpiperidin-4-ylmethoxy)pyrimidin-2-yl]benzyl}-6-oxo-1,6-dihydropyridazin-3-yl)benzonitrile, p-tosylate | or a tautomer or stereoisomer thereof,
wherein the pharmaceutical formulation is in the form of one or more dosage units, which is provided either as a single dose per day or in a series of doses of two or more per day so that the total daily dose would be the same as for the single dose per day, and
wherein said single or series of daily doses comprise 0.5 mg to 1 g of said active ingredient, or
0.1 to 100 mg of said active ingredient per kg of body weight of the intended recipient mammal.

2. A method according to claim 1, wherein the pharmaceutical composition is in the form of said single or series of daily doses and which comprise 1 mg to 700 mg of said active ingredient, or 1 to 10 mg of said active ingredient per kg of body weight of the intended recipient mammal.

3. A method according to claim 1, wherein the pharmaceutical composition is in the form of said single dose and which comprises 5 mg to 100 mg of said active ingredient.

4. A method according to claim 1, wherein the pharmaceutical composition contains 3-(1-{3-[5-(1-Methylpiperidin-4-ylmethoxy)pyrimidin-2-yl]benzyl}-6-oxo-1,6-dihydropyridazin-3-yl)benzonitrile, hydrochloride monohydrate.

5. A method according to claim 1, wherein said disease is a solid tumour.

6. A method according to claim 1, wherein said disease is a solid tumour which originates from the group consisting of tumors of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and the lung.

7. A method according to claim 1, wherein said disease is a solid tumour which originates from the group consisting of monocytic leukaemia, lung adenocarcinoma, small-cell lung carcinomas, pancreatic cancer, glioblastomas and breast carcinoma.

8. A method according to claim 1, wherein said disease is a solid tumour which originates from the group consisting of lung adenocarcinoma, small-cell lung carcinomas, pancreatic cancer, glioblastomas, colon carcinoma and breast carcinoma.

9. A method according to claim 1, wherein said disease is a tumour of the blood and immune system.

10. A method according to claim 1, wherein said disease is a tumour which originates from the group consisting of acute myeloid leukaemia, chronic myeloid leukaemia, acute lymphatic leukaemia and chronic lymphatic leukaemia.

11. A method according to claim 1, further comprising administering a pharmaceutically active compound, which is not a compound of claim 1.

12. A method according to claim 1, wherein the disease is a solid tumour which originates from the group consisting of tumors of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and the lung, or the disease is a solid tumour which originates from the group consisting of monocytic leukaemia, lung adenocarcinoma, small-cell lung carcinomas, pancreatic cancer, glioblastomas and breast carcinoma, or the disease is a solid tumour which originates from the group consisting of lung adenocarcinoma, small-cell lung carcinomas, pancreatic cancer, glioblastomas, colon carcinoma and breast carcinoma, or the disease is a tumour of the blood and immune system, or the disease is a tumour which originates from the group consisting of acute myeloid leukaemia, chronic myeloid leukaemia, acute lymphatic leukaemia and chronic lymphatic leukaemia.

13. A method according to claim 1, which is for treating a disease which is influenced by inhibition of Met kinase, wherein treating does not include prevention.

14. A method according to claim 13, wherein said disease is a solid tumour.

15. A method according to claim 13, wherein said disease is a solid tumour which originates from the group consisting of tumors of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and the lung.

16. A method according to claim 13, wherein said disease is a solid tumour which originates from the group consisting of monocytic leukaemia, lung adenocarcinoma, small-cell lung carcinomas, pancreatic cancer, glioblastomas, colon carcinoma and breast carcinoma.

17. A method according to claim 13, wherein said disease is a tumour of the blood and immune system.

18. A method according to claim 13, wherein said disease is a tumour which originates from the group consisting of acute myeloid leukaemia, chronic myeloid leukaemia, acute lymphatic leukaemia and chronic lymphatic leukaemia.

19. A method according to claim 1, which is for stabilizing or improving the clinical symptoms of a disease which is influenced by inhibition of Met kinase.

20. A method according to claim 19, wherein the disease is a solid tumour which originates from the group consisting of tumors of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and the lung, or the disease is a solid tumour which originates from the group consisting of monocytic leukaemia, lung adenocarcinoma, small-cell lung carcinomas, pancreatic cancer, glioblastomas and breast carcinoma, or the disease is a solid tumour which originates from the group consisting of lung adenocarcinoma, small-cell lung carcinomas, pancreatic cancer, glioblastomas, colon carcinoma and breast carcinoma, or the disease is a tumour of the blood and immune system, or the disease is a tumour which originates from the group consisting of acute myeloid leukaemia, chronic myeloid leukaemia, acute lymphatic leukaemia and chronic lymphatic leukaemia.

\* \* \* \* \*